(12) United States Patent
Hosokawa et al.

(10) Patent No.: US 11,434,213 B2
(45) Date of Patent: Sep. 6, 2022

(54) COMPLEX CRYSTAL AND CHEMOSENSOR PROVIDED WITH SAME

(71) Applicant: Panasonic Corporation, Kadoma (JP)

(72) Inventors: Teppei Hosokawa, Hyogo (JP);
Norimitsu Tohnai, Osaka (JP);
Mikihiko Nishitani, Osaka (JP)

(73) Assignee: PANASONIC HOLDINGS CORPORATION, Osaka (JP)

( * ) Notice: Subject to any disclaimer, the term of this patent is extended or adjusted under 35 U.S.C. 154(b) by 146 days.

(21) Appl. No.: 16/493,675

(22) PCT Filed: Mar. 15, 2018

(86) PCT No.: PCT/JP2018/010344
§ 371 (c)(1),
(2) Date: Sep. 12, 2019

(87) PCT Pub. No.: WO2018/169023
PCT Pub. Date: Sep. 20, 2018

(65) Prior Publication Data
US 2020/0010437 A1 Jan. 9, 2020

(30) Foreign Application Priority Data

Mar. 16, 2017 (JP) .............................. JP2017-051795

(51) Int. Cl.
*C07D 279/22* (2006.01)
*B01D 53/14* (2006.01)
*B01J 20/22* (2006.01)
*B01J 20/30* (2006.01)
*C07C 211/27* (2006.01)
*C07C 255/42* (2006.01)
*C07D 209/86* (2006.01)
*C07D 213/38* (2006.01)
*C07D 333/20* (2006.01)
*C07D 333/36* (2006.01)
*C09K 11/06* (2006.01)
*G01N 21/64* (2006.01)
*G01N 27/04* (2006.01)

(52) U.S. Cl.
CPC ........... *C07D 279/22* (2013.01); *B01D 53/14* (2013.01); *B01J 20/22* (2013.01); *B01J 20/30* (2013.01); *C07C 211/27* (2013.01); *C07C 255/42* (2013.01); *C07D 209/86* (2013.01); *C07D 213/38* (2013.01); *C07D 333/20* (2013.01); *C07D 333/36* (2013.01); *C09K 11/06* (2013.01); *G01N 21/64* (2013.01); *G01N 27/04* (2013.01)

(58) Field of Classification Search
CPC .. C07D 279/22; C07D 209/86; C07D 213/38; C07D 333/20; C07D 333/36; B01D 53/14; B01J 20/22; B01J 20/30; C07C 211/27; C07C 255/42; C09K 11/06; G01N 21/64; G01N 27/04
See application file for complete search history.

(56) References Cited

U.S. PATENT DOCUMENTS

| 2,906,773 | A | * | 9/1959 | Trapp | C07C 335/32 |
| | | | | | 558/4 |
| 5,196,147 | A | * | 3/1993 | Taketani | C07C 255/23 |
| | | | | | 252/582 |
| 2007/0134129 | A1 | * | 6/2007 | Maruo | G01N 21/783 |
| | | | | | 422/400 |
| 2013/0133433 | A1 | | 5/2013 | Yoshikawa et al. | |

FOREIGN PATENT DOCUMENTS

| EP | 0335641 A2 * | 10/1989 | ........... C07C 255/23 |
| JP | 02254425 A * | 10/1990 | |
| JP | H02254425 | 10/1990 | |
| JP | 03126925 A * | 5/1991 | |
| JP | 2009236607 | 10/2009 | |
| JP | 2015193563 | 11/2015 | |
| WO | 2011148774 | 12/2011 | |

OTHER PUBLICATIONS

A. Yamamoto et al., "Hierarchical Construction of Fluorescent Organic Porous Structures and Guest Responsive Fluorescent Modulation by Ammonium Carboxylates" Division of Organic Crystals Newsletter (with English-Language Translation), No. 29 (2011) (Year: 2011).*
Yamamoto, A., et al., "Hierarchical Construction of Fluorescent Organic Porous Structures and Guest Responsive Fluorescent Modulation by Ammonium Carboxylates," 7th Host-Guest Chemistry Symposium, Poster Presentation, Session ID: 1P-16 (with English-language Translation) (2011) (Year: 2011).*
T. Yuge et al., 13 Chem. Eur. J., 4163-4168 (2007) (Year: 2007).*
P. Hariharan et al., 17 Crystal Growth & Design, 146-155 (2017) (Year: 2017).*
N. Tohnai et al., 46 Angew. Chem. Int. Ed., 2220-2223 (2007) (Year: 2007).*
J. Mullin, in Ullmann's Encyclopedia of Industrial Chemistry, 581-630, 591 (2012) (Year: 2012).*
D Braga et al., Crystal Polymorphism and Multiple Crystal Forms, in 132 Molecular Networks: Structure Bonding, 25-50 (2009) (Year: 2009).*
International Search Report and Written Opinion issued for International Patent Application No. PCT/JP2018/010344, dated May 15, 2018, 9 pages including English translation of Search Report.

(Continued)

*Primary Examiner* — Alexander R Pagano
(74) *Attorney, Agent, or Firm* — Hamre, Schumann, Mueller & Larson, P.C.

(57) ABSTRACT

The complex crystal of the present disclosure is a complex crystal having a structure in which supramolecular units each composed of two or more types of molecules are arrayed. Each of the supramolecular units contains a cyanoacrylic acid derivative and a trisubstituted methylamine as the molecules. The complex crystal has, between the supramolecular units, molecular cavities in each of which a guest molecule for which the supramolecular unit is a host is not disposed. The complex crystal of the present disclosure can have a property of incorporating a chemical substance therein and can exhibit a great change in a characteristic when incorporating the chemical substance therein.

9 Claims, 13 Drawing Sheets

(56) References Cited

OTHER PUBLICATIONS

Yamamoto, A. et al., "Hierarchical Construction of Fluorescent Organic Porous Structures and Guest Responsive Fluorescent Modulation by Ammonium Carboxylates," Division of Organic Crystals Newsletter, No. 29, 2011, p. 59 (See English translation of International Search Report for relevance).

Hariharan, P. S. et al., "Molecular Engineering of Triphenylamine Based Aggregation Enhanced Emissive Fluorophore: Structure-Dependent Mechanochromism and Self-Reversible Fluorescence Switching," Crystal Growth & Design, vol. 17, No. 1, 2016, pp. 146-155.

Yamamoto, A., et al., "Hierarchical Construction of Fluorescent Organic Porous Structures and Guest Responsive Fluorescent Modulation by Ammonium Carboxylates," 7th Host-Guest Chemistry Symposium, Poster Presentation, Session ID: 1P-16, 2011 (See English translation of Specification for relevance).

Extended European Search Report issued for European Patent Application No. 18768431.1, dated Feb. 17, 2020, 3 pages.

Anthony, S. P. et al., "Impact of molecular structure on intermolecular interactions and organic solid state luminescence in supramolecular systems," J. Phys. Org. Chem., 2010, 23, 1074-1079.

* cited by examiner

COMPLEX CRYSTAL AND CHEMOSENSOR PROVIDED WITH SAME

TECHNICAL FIELD

The present disclosure relates to a complex crystal and a chemosensor including the complex crystal.

BACKGROUND ART

A complex crystal is a crystal composed of two or more types of molecules. A complex crystal has a structure in which molecules are arrayed by non-covalent interactions. Examples of the interactions include hydrogen bonds, ionic bonds, and Π-Π interactions. The force acting between molecules by these interactions is weaker than that by covalent bonds.

One type of complex crystal has a structure in which supramolecular units and guest molecules for which the supramolecular units are hosts are arrayed. Each supramolecular unit is composed of two or more types of molecules. This crystal has a hierarchical structure of primary and secondary structures. The primary structure is an array of the two or more types of molecules forming the supramolecular unit. The secondary structure is an array of the guest molecules and the supramolecular units forming the complex crystal. Each of the arrays is based on non-covalent interactions. The term "supramolecular unit" reflects the primary and secondary structures. Specifically, the "supramolecule" reflects the primary structure, which is an array of the two or more types of molecules by non-covalent bonds. The "unit" reflects that this supramolecule is one unit of the secondary structure forming the complex crystal.

One example of the supramolecular units is an organic salt of an anion that is an organic acid and a cation that is a protonated base. In this example, an ionic bond acts between the anion and the cation. An example of the organic acid is sulfonic acid. An example of the base is an amine.

A complex crystal of guest molecules and supramolecular units that are an organic salt can be formed, for example, by the following methods. One of the methods is a method of recrystallizing the organic salt with a solvent that is the guest molecules. In this method, at the time of recrystallization, the organic salt is arrayed as the supramolecular units while including the guest molecules. Another one of the methods is a method of exposing the organic salt to vapor of the guest molecules. In this method, as a result of the exposure, the organic salt is arrayed as the supramolecular units while including the guest molecules.

Patent Literature 1, which is a previous application of one of the applicants, discloses a complex crystal having supramolecular units that are an organic salt of an aromatic sulfonic acid and an aromatic amine. Patent Literature 1 also discloses a method of exposing a shaped body of the organic salt to vapor of guest molecules to obtain a complex crystal.

Non Patent Literature 1, which was disclosed by the other of the applicants, discloses a complex crystal having supramolecular units that are an organic salt of (4-diphenylamino)phenylcyanoacrylic acid and triphenylmethylamine with a specific binding ratio. Non Patent Literature 1 indicates that the fluorescence spectrum exhibited by the complex crystal varies depending on the type of guest molecules. Non Patent Literature 1 describes "As a result of recrystallization with various organic solvents, crystals exhibiting fluorescence from blue to orange were obtained. Measurements such as thermal analysis revealed that all crystals except the crystal exhibiting orange fluorescence were crystals including the recrystallization solvents as guests." The crystal exhibiting orange fluorescence and not including the recrystallization solvent as a guest is a crystal composed of only (4-diphenylamino)phenylcyanoacrylic acid and is not a complex crystal.

CITATION LIST

Patent Literature

Patent Literature 1: Japanese Laid-Open Patent Publication No. 2015-193563

Non Patent Literature

Non Patent Literature 1: "Hierarchical Construction of Fluorescent Organic Porous Structures and Guest Responsive Fluorescent Modulation by Ammonium Carboxylates", Atsushi Yamamoto, et al., 7th Host-Guest Chemistry Symposium (2011), Poster Presentation, Session ID: 1P-16

SUMMARY OF INVENTION

Technical Problem

The present disclosure provides a complex crystal that can have a property of incorporating a chemical substance therein and that can exhibit a great change in a characteristic when incorporating the chemical substance therein.

Solution to Problem

The present disclosure provides a complex crystal having a structure in which supramolecular units each composed of two or more types of molecules are arrayed, wherein
each of the supramolecular units contains a cyanoacrylic acid derivative and a trisubstituted methylamine as the molecules, and
the complex crystal includes, between the supramolecular units, molecular cavities in each of which a guest molecule for which the supramolecular unit is a host is not disposed.

According to another aspect, the present disclosure provides a method for producing the complex crystal of the present disclosure, the method including
detaching the guest molecules from a precursor complex crystal having a structure in which the supramolecular units and the guest molecules are arrayed, to form the complex crystal, wherein
the detachment of the guest molecules from the precursor complex crystal is carried out by supercritical drying using supercritical carbon dioxide.

Advantageous Effects of Invention

The complex crystal of the present disclosure can have a property of incorporating a chemical substance therein and can exhibit a great change in a characteristic when incorporating the chemical substance therein.

Figure 1:
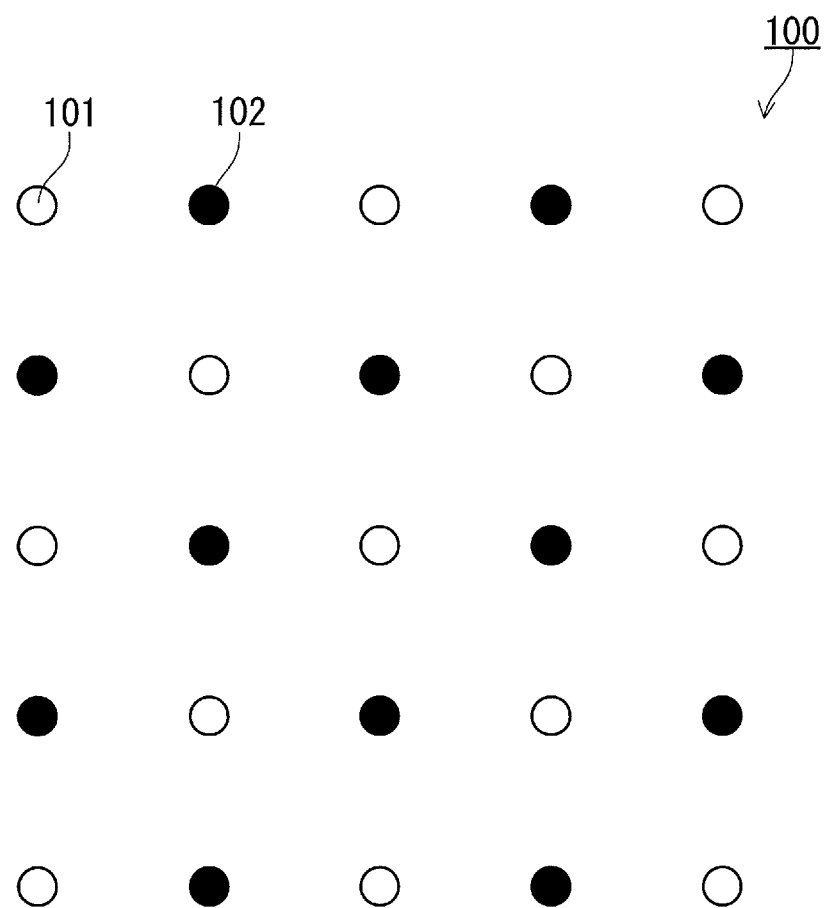
FIG. 1 is a schematic diagram for explaining a conventional complex crystal.

DESCRIPTION OF EMBODIMENTS (Circumstances of Reaching One Aspect of Present Disclosure)

A complex crystal of supramolecular units and guest molecules can have a property of incorporating a chemical substance therein and a property of a characteristic thereof changing when incorporating the chemical substance therein. Application of the complex crystal having these properties to a sensor that detects a chemical substance (hereinafter, simply "chemosensor") has been attempted. Patent Literature 1 discloses a chemosensor including a complex crystal of a specific organic salt. In the chemosensor, the degree of a change in the characteristic corresponds to the sensitivity to the chemical substance. However, the sensitivity exhibited by the conventional complex crystal is not sufficient. The conventional complex crystal does not have, for example, sensitivity to the chemical substance at a low concentration. The change in fluorescence spectrum indicated in Non Patent Literature 1 is not attributed to incorporation of the chemical substance into the complex crystal. This change is based on the difference in guest molecules forming the crystal.

According to the study by the present inventors, the complex crystal of Patent Literature 1 exhibits a small change in a characteristic when incorporating the chemical substance therein. More specifically, the complex crystal of Patent Literature 1 does not have sensitivity to the chemical substance at a low concentration such as a ppm level. Thus, this crystal is not suitable for a chemosensor that detects the chemical substance at a low concentration. An example of the chemosensor that detects the chemical substance at a low concentration is a chemosensor for an exhaled chemical substance and/or a skin chemical substance.

According to the study by the present inventors, complex crystals of Non Patent Literature 1 has a possibility of having a property of incorporating a chemical substance therein and having sensitivity to the chemical substance at a low concentration. This is because disruption of the electronic structure of (4-diphenylamino)phenylcyanoacrylic acid by the chemical substance may cause great light emission modulation. However, the guest molecules forming the crystal decreases the sensitivity to the chemical substance. It is inferred that the guest molecules inhibit incorporation of the chemical substance. The complex crystal of Non Patent Literature 1 does not have the molecular cavities described above.

The present inventors have found that a complex crystal that can exhibit a great change in a characteristic when incorporating a chemical substance therein is achieved by:

(1) having a structure in which supramolecular units each composed of two or more types of molecules are arrayed;

(2) each supramolecular unit containing a cyanoacrylic acid derivative and a trisubstituted methylamine as the molecules forming the unit; and (3) having, between the supramolecular units, molecular cavities in each of which a guest molecule for which the supramolecular unit is a host is not disposed.

The complex crystal of the present disclosure can have higher sensitivity to a chemical substance than the conventional complex crystals. This crystal has, for example, sensitivity to the chemical substance at a low concentration. With the complex crystal of the present disclosure, a chemosensor having sensitivity to the chemical substance at a low concentration can be achieved.

(Aspects of Disclosure)

A complex crystal of a first aspect of the present disclosure has a structure in which supramolecular units each composed of two or more types of molecules are arrayed. Each of the supramolecular units contains a cyanoacrylic acid derivative and a trisubstituted methylamine as the molecules. The complex crystal has, between the supramolecular units, molecular cavities in each of which a guest molecule for which the supramolecular unit is a host is not disposed.

In a second aspect of the present disclosure, for example, the complex crystal of the first aspect does not substantially contain the guest molecule. According to the second aspect, the above-described effects are more assuredly achieved.

In a third aspect of the present disclosure, for example, in the complex crystal of the first or second aspect, the cyanoacrylic acid derivative is a compound represented by the following formula (1).

[Chem. 1]

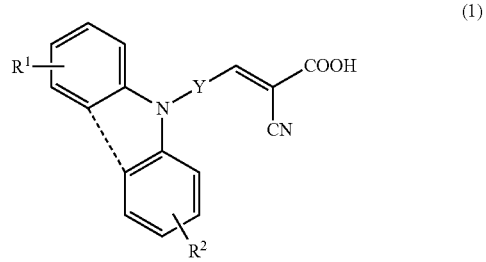

(1)

wherein Y is a phenylene group, a naphthylene group, a pyridinylene group, a thiophenylene group, or a furanylene group, each group may have a substituent, $R^1$ and $R^2$ are each independently a hydrogen atom, a hydroxyl group, a methoxy group, an ethoxy group, a methyl group, an ethyl group, a propyl group, an isopropyl group, an amino group, a cyano group, an aldehyde group, a thiol group, a vinyl group, a nitro group, a halogen atom, a carboxy ester group, an N-substituted amide group, a phenyl group, a naphthyl group, a pyridyl group, a thiophenyl group, or a furanyl group, the compound represented by formula (1) may or may not have a bond at a broken line portion in formula (1), and, when the compound has the bond, the bond is a single bond, —$CH_2$—, —O—, —S—, or —NH—.

In a fourth aspect of the present disclosure, for example, in the complex crystal of any one of the first to third aspects, the trisubstituted methylamine is a compound represented by the following formula (2).

[Chem. 2]

(2)

wherein $R^3$ to $R^5$ are each independently a phenyl group, a naphthyl group, a pyridyl group, a thiophenyl group, or a furanyl group, and each group may have a substituent.

In a fifth aspect of the present disclosure, for example, the complex crystal of any one of the first to fourth aspects is a complex crystal obtained by detaching the guest molecules from a precursor complex crystal having a structure in which the supramolecular units and the guest molecules are arrayed, by supercritical drying using supercritical carbon dioxide.

A chemosensor of a sixth aspect of the present disclosure includes, for example, the complex crystal of any one of the first to fifth aspects and a detection unit configured to detect a characteristic of the complex crystal. The chemosensor detects a predetermined chemical substance on the basis of a change in the characteristic detected by the detection unit.

In a seventh aspect of the present disclosure, for example, in the chemosensor of the sixth aspect, the detection unit includes a light source configured to irradiate the complex crystal with light, and a light detector configured to detect light emitted from the complex crystal. With the light emitted from the complex crystal as the characteristic, the chemosensor detects the predetermined chemical substance on the basis of a change in the light.

In an eighth aspect of the present disclosure, for example, in the chemosensor of the seventh aspect, the change in the light is a difference between light emitted from the complex crystal in a first environmental condition and light emitted from the complex crystal in a second environmental condition.

A production method of a ninth aspect of the present disclosure is, for example, a method for producing the complex crystal according to any one of the first to fourth aspects, the method including detaching the guest molecules from a precursor complex crystal having a structure in which the supramolecular units and the guest molecules are arrayed, to form the complex crystal, wherein the detachment of the guest molecules from the precursor complex crystal is carried out by supercritical drying using supercritical carbon dioxide.

[Complex Crystal]

Hereinafter, the complex crystal of the present disclosure will be described with reference to the drawings.

FIG. 1 is a schematic diagram for explaining a conventional complex crystal. In a structure 100 of the conventional complex crystal, supramolecular units 101 and guest molecules 102 for which the supramolecular units 101 are hosts are arrayed. The supramolecular units 101 and the guest molecules 102 are arrayed by non-covalent interactions. Examples of the interactions include hydrogen bonds, ionic bonds, CH-Π interactions, halogen-Π interactions, halogen-halogen interactions, van der Waals interactions, and Π-Π interactions.

Figure 2:
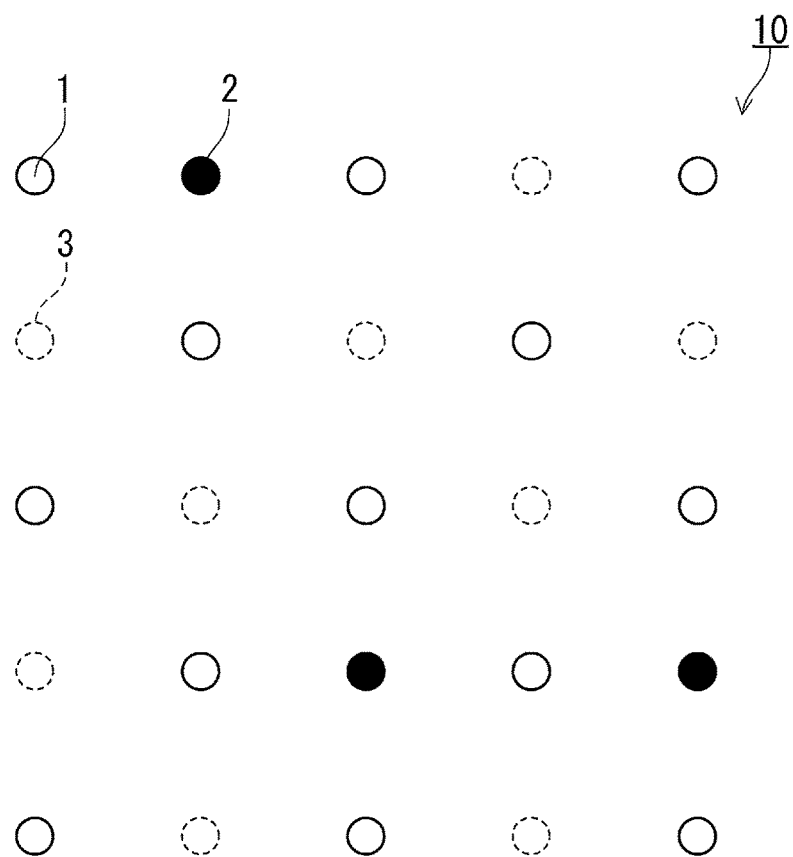
FIG. 2 is a schematic diagram for explaining the complex crystal of the present disclosure.

FIG. 2 is a schematic diagram for explaining the complex crystal of the present disclosure. In a structure 10 of the complex crystal of the present disclosure, supramolecular units 1 are arrayed by non-covalent interactions. The structure 10 has, between the supramolecular units 1, molecular cavities 3 in each of which a guest molecule 2 for which the supramolecular unit 1 is a host is not disposed. The molecular cavities 3 are not spaces within the supramolecular unit 1.

In the structure 10, an array of the supramolecular units 1 and the guest molecules 2 and/or the molecular cavities 3 can be further established.

The structure 10 can be a structure in which the guest molecules 102 are detached from the structure 100 in FIG. 1. In this case, the molecular cavities 3 are empty sites formed by the detachment of the guest molecules 102. It should be noted that the array of the supramolecular units 101 before the detachment and the array of the supramolecular units 1 after the detachment may be different from each other. This is because the array of the supramolecular units may change when the guest molecules 102 are detached.

The structure 10 in FIG. 2 merely schematically represents an example of an array that the complex crystal of the present disclosure has. A specific array of the supramolecular units 1 in the complex crystal of the present disclosure is not limited.

The molecular cavities 3 can have a specific array. For example, the molecular cavities 3 can be arrayed in the form of channels or layers in the crystal.

The composition ratio of the supramolecular units 1, the guest molecules 2, and the molecular cavities 3 in the complex crystal of the present disclosure is not limited.

The content of the guest molecules 2 in the complex crystal of the present disclosure is not limited, as long as the complex crystal has the molecular cavities 3. In the present specification, the content of the guest molecules 2 in the complex crystal means the ratio of the number of the guest molecules 2 to the number of cyanoacrylic acid derivative molecules. The content of the guest molecules 2 is, for example, equal to or less than 30 mol %. The content of the guest molecules 2 can be equal to or less than 10 mol % and further equal to or less than 5 mol %. The content of the guest molecules 2 can be evaluated by thermogravimetric analysis, nuclear magnetic resonance (NMR) measurement, mass spectrometry, or the like on the complex crystal.

The complex crystal of the present disclosure need not substantially contain guest molecules 2. In the present specification, "not substantially containing" means a content equal to or less than 1 mol %. Since the measurement limit of content by NMR is 1 mol %, a content less than 1 mol % may be defined as "not substantially containing".

A cavity rate in the complex crystal of the present disclosure (the ratio of the number of the molecular cavities 3 to the sum of the number of the guest molecules 2 and the number of the molecular cavities 3) is, for example, equal to or greater than 70%, and may be equal to or greater than 90%, equal to or greater than 95%, and further equal to or greater than 99%. The cavity rate can be evaluated by thermogravimetric analysis, NMR measurement, mass spectrometry, or the like on the complex crystal.

The content of the guest molecules 2 can be controlled, for example, by a method and a condition for detaching the guest molecules 2 in a production method described later. An example of the condition is at least one selected from temperature, time (speed), pressure, and type of supercritical fluid.

The array of the supramolecular units 1, the guest molecules 2, and the molecular cavities 3, that is, the crystal structure, can be evaluated by X-ray diffraction (XRD) measurement or the like on the complex crystal.

The array of the supramolecular units 1, the guest molecules 2, and the molecular cavities 3 can be controlled, for example, by a condition for coagulation, recrystallization, or exposure and the method and the condition for detaching the guest molecules 2 in the production method described later. An example of the condition is at least one selected from temperature, time (speed), pressure, type of supercritical fluid, and type and mixing ratio of solvent to be used for recrystallization or coagulation.

Each supramolecular unit 1 is composed of two or more types of molecules. Each supramolecular unit 1 can be composed of two types of molecules. In each supramolecular unit 1, two or more types of molecules are arrayed by non-covalent interactions. The complex crystal of the present disclosure has a hierarchical structure of primary and secondary structures. The primary structure is an array of the two or more types of molecules forming the supramolecular unit 1. The secondary structure is the structure 10 in which the supramolecular units 1 are arrayed.

Figure 3:
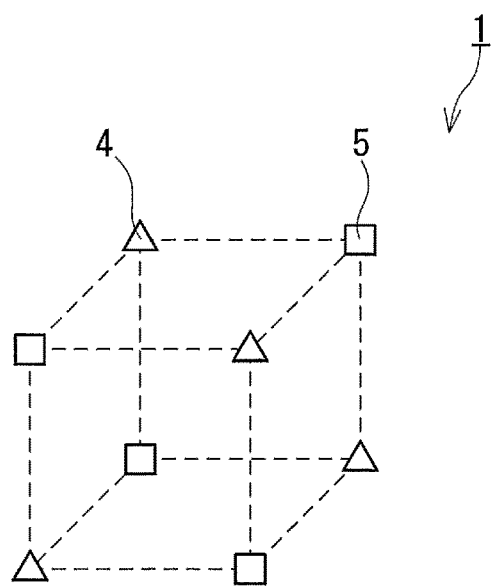
FIG. 3 is a schematic diagram for explaining a supramolecular unit.

FIG. 3 is a schematic diagram for explaining an example of the array of the molecules in the supramolecular units 1. In the supramolecular unit 1 in FIG. 3, two types of molecules, molecules 4 and molecules 5, are arrayed. The binding ratio between the molecules 4 and the molecules 5 in the supramolecular unit 1 in FIG. 3 is 4:4. In other words, an array of four molecules 4 and four molecules 5 forms one supramolecular unit 1.

The supramolecular units 1 of the complex crystal of the present disclosure contain a cyanoacrylic acid derivative and a trisubstituted methylamine. In each supramolecular unit 1, the cyanoacrylic acid derivative and the trisubstituted methylamine are arrayed at a predetermined binding ratio. Each supramolecular unit 1 is an organic salt of the cyanoacrylic acid derivative and the trisubstituted methylamine Molecules of both compounds are arrayed by ionic bonds.

A binding ratio x:y between the cyanoacrylic acid derivative and the trisubstituted methylamine in the supramolecular unit 1 is not limited, as long as the cyanoacrylic acid derivative and the trisubstituted methylamine can form an organic salt. Each of x and y is, for example, an integer equal to or greater than 1, and the upper limit thereof is, for example, 10, and may be 6. The binding ratio is, for example, an integer of 1 to 6: an integer of 1 to 6. The binding ratio can be 1:1, 2:2, 3:3, 4:4, 5:5, or 6:6.

The binding ratio of the molecules in the supramolecular unit 1 can be evaluated by XRD measurement or the like on the complex crystal.

The binding ratio of the molecules in the supramolecular unit 1 can be controlled by the condition for coagulation, recrystallization, or exposure in the production method described later. An example of the condition is at least one selected from temperature, time (speed), pressure, and type and mixing ratio of solvent to be used for recrystallization or coagulation.

Each supramolecular unit 1 can contain a third molecule other than the cyanoacrylic acid derivative and the trisubstituted methylamine. The third molecule, together with the cyanoacrylic acid derivative and the trisubstituted methylamine, can form an array of the supramolecular unit 1.

The complex crystal of the present disclosure can contain two or more types of supramolecular units 1.

The compositions of the complex crystal and the supramolecular units 1 and the binding ratio of the molecules forming the supramolecular unit 1 can be evaluated, for example, by NMR measurement and/or XRD measurement.

<Cyanoacrylic Acid Derivative>

The cyanoacrylic acid derivative has a structure in which a substituent is bound to the carbon atom at the β position in the vinyl group of cyanoacrylic acid. The substituent can have a molecule structure that allows the cyanoacrylic acid derivative to exhibit fluorescence and that allows the complex crystal to exhibit a change in fluorescence due to incorporation of a chemical substance. The change in fluorescence due to incorporation of the chemical substance can be used for detection of the chemical substance in a chemosensor. The fluorescence is, for example, a characteristic of emitting fluorescence in the wavelength band of 400 to 700 nm by excitation with ultraviolet light.

The cyanoacrylic acid derivative can be a compound represented by the following formula (1). In formula (1), Y is a phenylene group, a naphthylene group, a pyridinylene group, a thiophenylene group, or a furanylene group, and each group may have a substituent. $R^1$ and $R^2$ are each independently a hydrogen atom, a hydroxyl group, a methoxy group, an ethoxy group, a methyl group, an ethyl group, a propyl group, an isopropyl group, an amino group, a cyano group, an aldehyde group, a thiol group, a vinyl group, a nitro group, a halogen atom, a carboxy ester group (—COOR$^6$), an N-substituted amide group (—CONHR$^7$), a phenyl group, a naphthyl group, a pyridyl group, a thiophenyl group, or a furanyl group. The compound represented by formula (1) need not have a bond at a broken line portion in formula (1). In the case where the compound has a bond at the broken line portion, the bond is a single bond, —CH$_2$— (methylene group), —O— (ether bond), —S— (sulfide bond), or —NH—(imino group).

[Chem. 3]

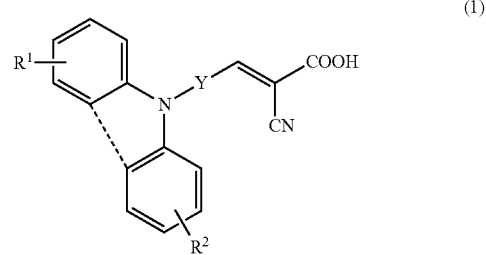

(1)

The compound represented by formula (1) need not have a bond at the broken line portion, or may have a single bond at the broken line portion. Y may be a phenylene group, a naphthylene group, or a pyridinylene group. $R^1$ and $R^2$ may each independently be a hydrogen atom, a methoxy group, a methyl group, an ethyl group, a propyl group, or an isopropyl group.

The substituent that Y can have is, for example, the group exemplified as $R^1$ and $R^2$. The substituent may be a hydrogen atom, a methoxy group, a methyl group, an ethyl group, a propyl group, or an isopropyl group. $R^6$ is, for example, a methyl group, an ethyl group, a propyl group, or an isopropyl group. $R^7$ is, for example, a methyl group, an ethyl group, a propyl group, an isopropyl group, or a phenyl group.

Figure 4:
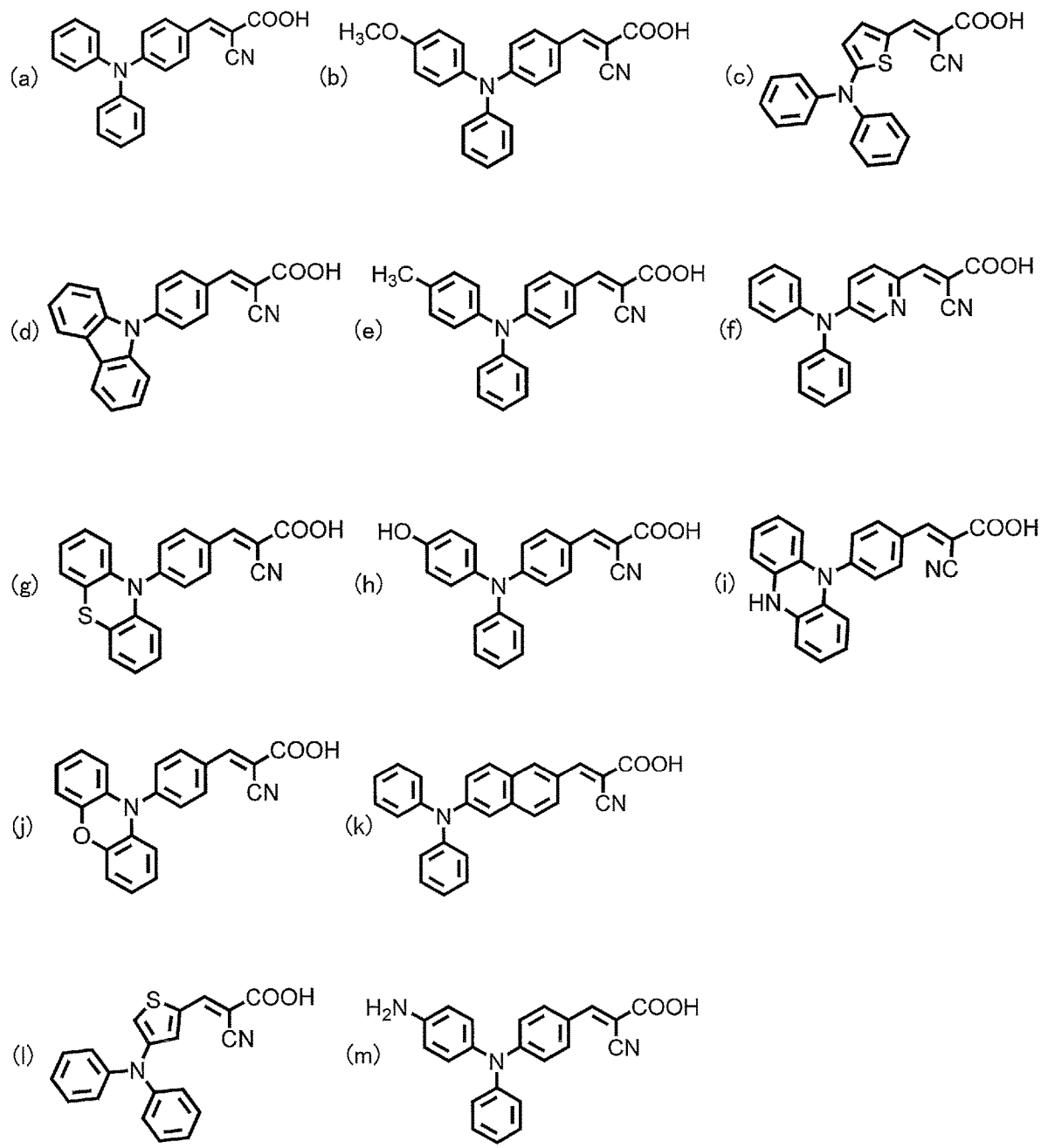
FIG. 4 shows examples of a cyanoacrylic acid derivative that can form the supramolecular unit of the complex crystal according to the present disclosure.

FIG. 4 shows examples of the cyanoacrylic acid derivative forming each supramolecular unit of the complex crystal according to the present disclosure. The examples in FIG. 4 are, in the order of (a) to (m), (E)-2-cyano-3-(4-(diphenylamino)phenyl)acrylic acid, (E)-2-cyano-3-(4-((4-methoxyphenyl)(phenyl)amino)phenyl)acrylic acid, (E)-2-cyano-3-(5-(diphenylamino)thiophen-2-yl)acrylic acid, (E)-3-(4-(9H-carbazol-9-yl)phenyl)-2-cyanoacrylic acid, (E)-2-cyano-3-(4-(phenyl(para-tolyl)amino)phenyl)acrylic acid, (E)-2-cyano-3-(5-(diphenylamino)pyridin-2-yl) acrylic acid, (E)-3-(4-(10H-phenothiazine-10-yl)phenyl)-2-cyanoacrylic acid, (E)-2-cyano-3-(4-((4-hydroxyphenyl)(phenyl)amino)phenyl)acrylic acid, (E)-2-cyano-3-(4-(phenazine-5(10H)-yl)phenyl)acrylic acid, (E)-3-(4)-(10H-phenoxazin-10-yl)phenyl)-2-cyanoacrylic acid, (E)-2-cyano-3-(6-(diphenylamino)naphthalen-2-yl)acrylic acid, (E)-2-cyano-3-(4-(diphenylamino)thiophen-2-yl)acrylic acid, and (E)-3-(4-((4-aminophenyl)(phenyl)amino)phenyl)-2-cyanoacrylic acid.

<Trisubstituted Methylamine>

The trisubstituted methylamine has a structure in which the three hydrogen atoms bound to the methyl group of methylamine are substituted by substituents. All the three substituents may be identical, two of the three substituents may be identical, or all the three substituents may be different from each other.

The trisubstituted methylamine can be a compound represented by the following formula (2). In formula (2), $R^3$ to $R^5$ are each independently a phenyl group, a naphthyl group, a pyridyl group, a thiophenyl group, or a furanyl group, and each group may have a substituent. $R^3$ to $R^5$ may each independently be a phenyl group, a pyridyl group, or a thiophenyl group. Each of the substituents that $R^3$ to $R^5$ can have is, for example, the group exemplified as $R^1$ and $R^2$. The substituent may be a hydrogen atom, a methoxy group, a methyl group, an ethyl group, a propyl group, an isopropyl group, or a halogen atom.

[Chem. 4]

(2)

Figure 5:
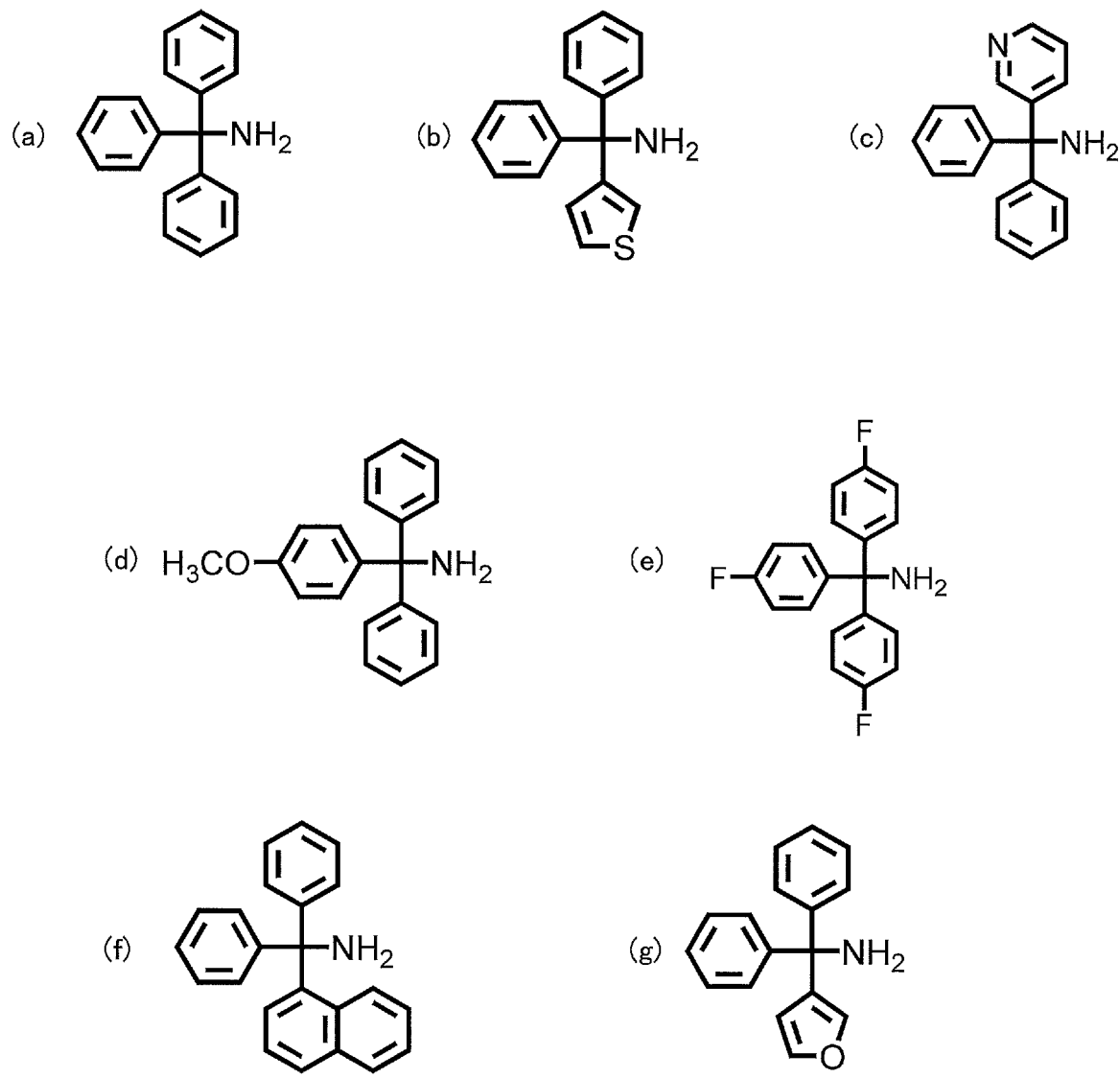
FIG. 5 shows examples of a trisubstituted methylamine that can form the supramolecular unit of the complex crystal according to the present disclosure.

FIG. 5 shows examples of the trisubstituted methylamine forming each supramolecular unit of the complex crystal according to the present disclosure. The examples in FIG. 5 are, in the order of (a) to (g), triphenylmethylamine, diphenyl(thiophen-3-yl)methylamine, diphenyl(pyridin-3-yl) methylamine, (4-methoxyphenyl)diphenylmethylamine, tris(4-fluorophenyl)methylamine, naphthalen-1-yl diphenylmethylamine, and furan-3-yl diphenylmethylamine <Guest Molecules>

In the case where the complex crystal of the present disclosure contains guest molecules 2, the guest molecules 2 are not limited. The guest molecules 2 are, for example, a compound capable of forming a later-described precursor complex crystal by combination with the organic salt of the cyanoacrylic acid derivative and the trisubstituted methylamine.

The guest molecules 2 can be a compound that defines the sizes and/or the shapes of the molecular cavities 3, as a template molecule when constructing the complex crystal of the present disclosure.

The guest molecules 2 can be a solvent for recrystallization in the production method described later, or a compound that can be used for exposure of the organic salt.

The guest molecules 2 are, for example, water, n-pentane, n-hexane, cyclohexane, n-heptane, n-octane, methylcyclohexane, methanol, ethanol, isopropanol (also referred to as "1-methylethanol"), 1-propanol, 1-butanol, 2-butanol, isobutanol (also referred to as "2-methylpropanol"), t-butanol, acetone, methyl ethyl ketone (also referred to as "2-butanone"), methyl propyl ketone (also referred to as "2-pentanone"), methyl isopropyl ketone, methyl butyl ketone, methyl isobutyl ketone, diethyl ketone, methyl amyl ketone (also referred to as "methyl-n-pentyl ketone"), methyl-t-butyl ketone (also referred to as "pinacolone"), benzaldehyde, butylaldehyde, methyl acetate, ethyl acetate, propyl acetate, butyl acetate, methyl benzoate, ethyl benzoate, dimethyl phthalate, ethyl cinnamate, diethyl ether, diisopropyl ether, t-butyl methyl ether, benzene, toluene, o-xylene, m-xylene, p-xylene, chlorobenzene, o-chlorotoluene, m-chlorotoluene, p-chlorotoluene, o-dichlorobenzene, m-dichlorobenzene, p-dichlorobenzene, anisole, ethylbenzene, 1,2-diethylbenzene, 1,4-diethylbenzene, 1,3,5-trimethylbenzene (also referred to as "mesitylene"), 1,3-diisopropylbenzene, n-octylbenzene, nitrobenzene, benzonitrile, dichloromethane, 1,2-dichloroethane, chloroform, monofluorobenzene, 1,2-difluorobenzene, 1,3-difluorobenzene, 1,4-difluorobenzene, 1,3,5-trifluorobenzene, hexafluorobenzene, acrylonitrile, acetonitrile, N,N-dimethylformamide, N,N-dimethylacetamide, N-methyl-2-pyrrolidone, N,N-dimethylamine, N,N-diethylamine, N,N-di-n-propylamine, N,N-diisopropylamine, N,N-dibutylamine, N,N-dimethyl-o-toluidine, N,N-dimethyl-m-toluidine, N,N-dimethyl-p-toluidine, N,N-diethyl-o-toluidine, N,N-diethyl-m-toluidine, N,N-diethyl-p-toluidine, pyridine, piperidine, 1-methylpiperidine, pyrimidine, pyridazine, pyrazine, piperazine, α-picoline, β-picoline, γ-picoline, aniline, N,N-dimethylaniline, dimethylsulfoxide, and sulfolane.

The complex crystal of the present disclosure can contain two or more types of guest molecules 2.

The form of the complex crystal of the present disclosure is not limited. The complex crystal of the present disclosure can have various forms such as particles, films, sheets, bulks, thin films, and monoliths. In the complex crystal having these various forms, the distribution of the molecular cavities 3 may be uniform, or may be non-uniform.

The size of the complex crystal of the present disclosure is not limited. The size can take a wide range from a macro area such as bulk and monolith to a micro area represented by a thin film forming an element on a circuit board.

Application of the complex crystal of the present disclosure is not limited. An example of the application is a chemosensor that detects a chemical substance. The chemosensor uses a change in a crystal characteristic due to incorporation of the chemical substance. The characteristic is, for example, an absorption spectrum, a reflection spectrum, a fluorescence spectrum, an electrical characteristic, and mass. The state of change in the characteristic can vary depending on the type of the chemical substance incorporated. By using this, it is possible to configure a chemosensor that further detects the type of the chemical substance.

[Production Method for Complex Crystal]

The complex crystal of the present disclosure can be formed, for example, by detaching the guest molecules 2 from a precursor complex crystal having a structure in which the supramolecular units 1 and the guest molecules 2 are arrayed. The precursor complex crystal can have the structure 100 in FIG. 1. The precursor complex crystal can be a crystal that does not include the molecular cavities 3.

The method for detaching the guest molecules 2 is not limited. An example of the detaching method is heating and/or depressurization. A method of replacing the guest molecules 2 with another compound and detaching the replaced other compound can also be adopted. The other compound can be a compound that is more easily detached than the guest molecules 2.

Another example of the method for detaching the guest molecules 2 is supercritical drying. The detachment by supercritical drying can suppress structural destruction of the complex crystal at the time of the detachment of the guest molecules 2 and deformation associated therewith, as compared to the detachment by simple heating and/or depressurization. In the detachment by supercritical drying, the array of the supramolecular units 1 can be more assuredly maintained before and after the detachment of the guest molecules 2. In the detachment by supercritical drying, the form of the complex crystal can be more assuredly maintained before and after the detachment of the guest molecules 2. These effects are based on the high diffusivity and solubility of a supercritical fluid and its surface tension which is zero.

An example of the fluid to be used for supercritical drying is carbon dioxide in a supercritical state (supercritical carbon dioxide).

The precursor complex crystal can be formed, for example, by the following methods.

<First Method>

A first method is a method of recrystallizing the organic salt of the cyanoacrylic acid derivative and the trisubstituted methylamine with a solvent that is the guest molecules 2. In this method, as a result of the recrystallization, the organic salt is arrayed as the supramolecular units 1 while including the guest molecules 2. Because of the array, the precursor complex crystal is formed.

The organic salt to be recrystallized can be formed, for example, by coagulating a mixture of the cyanoacrylic acid derivative and the trisubstituted methylamine with a solvent. The solvent is a compound that is capable of coagulating the organic salt. The solvent need not be the guest molecules 2.

The first method can be carried out according to a known method for forming a complex crystal by recrystallization of an organic salt. It should be noted that, in the first method, the organic salt of the cyanoacrylic acid derivative and the trisubstituted methylamine is recrystallized.

The first method and detachment of the guest molecules 2 can be continuously carried out.

<Second Method>

A second method is a method of exposing the organic salt of the cyanoacrylic acid derivative and the trisubstituted methylamine to vapor of the guest molecules 2. In this method, as a result of the exposure, the organic salt is arrayed as the supramolecular units 1 while including the guest molecules 2. Because of the array, the precursor complex crystal is formed.

The second method can be carried out according to a known method for forming a complex crystal by exposing an organic salt to vapor of the guest molecules 2. It should be noted that, in the second method, the organic salt of the cyanoacrylic acid derivative and the trisubstituted methylamine is exposed.

The organic salt to be exposed can be formed, for example, by coagulating a mixture of the cyanoacrylic acid derivative and the trisubstituted methylamine with a solvent. The solvent is a compound that is capable of coagulating the organic salt. The solvent need not be the guest molecules 2. In this method, it is possible to shape the organic salt at the time of coagulation or after coagulation. A shaped body of the organic salt can be formed, for example, by preparing a solution or a dispersion liquid of the coagulated organic salt and applying the solution or the dispersion liquid to a substrate by a method such as spin coating, dispenser, inkjet, and 3D printing. In addition, by selecting an exposure method, the form of the shaped organic salt can be maintained before and after exposure.

The second method and detachment of the guest molecules 2 can be continuously carried out.

The form of the finally obtained complex crystal can be controlled, for example, by the following methods.

Filling a container with the complex crystal. The container can be a container to be used when the complex crystal is used in a predetermined application. An example of the container is a narrow tube of glass or the like. The complex crystal filled in the narrow tube can be used, for example, for a gas detection tube which is one type of chemosensor.

Preparing a solution or a dispersion liquid of the complex crystal and applying the solution or the dispersion liquid to a substrate by a method such as spin coating, dispenser, inkjet, and 3D printing.

Placing a slurry containing the complex crystal, a dispersant, and a binder on a substrate and drying and solidifying the slurry.

Figure 6:
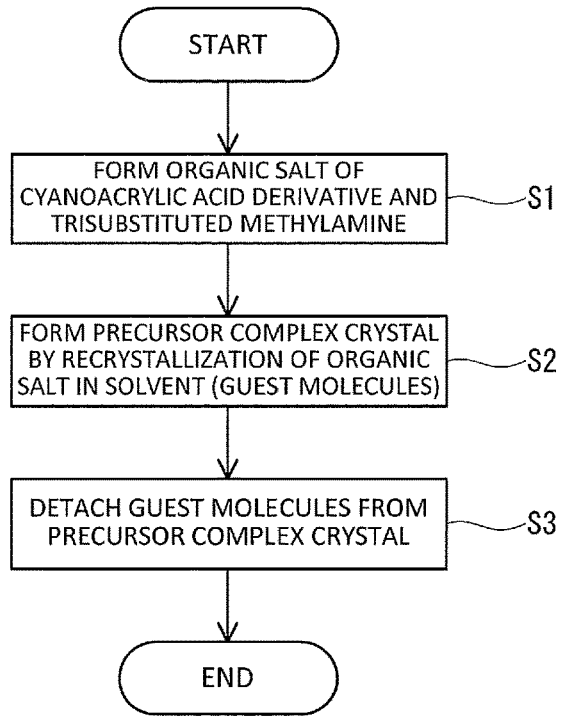
FIG. 6 shows an example of a method for producing the complex crystal according to the present disclosure.

FIG. 6 shows an example of the method for producing the complex crystal of the present disclosure. The method in FIG. 6 includes the following steps S1, S2 and S3. Step S1 is a step of forming the organic salt of the cyanoacrylic acid derivative and the trisubstituted methylamine. Step S2 is a step of forming a precursor complex crystal by recrystallizing the organic salt formed in step S1 with a solvent that is the guest molecules 2. Step S3 is a step of forming the complex crystal of the present disclosure by detaching the guest molecules 2 from the precursor complex crystal formed in step S2.

Figure 7:
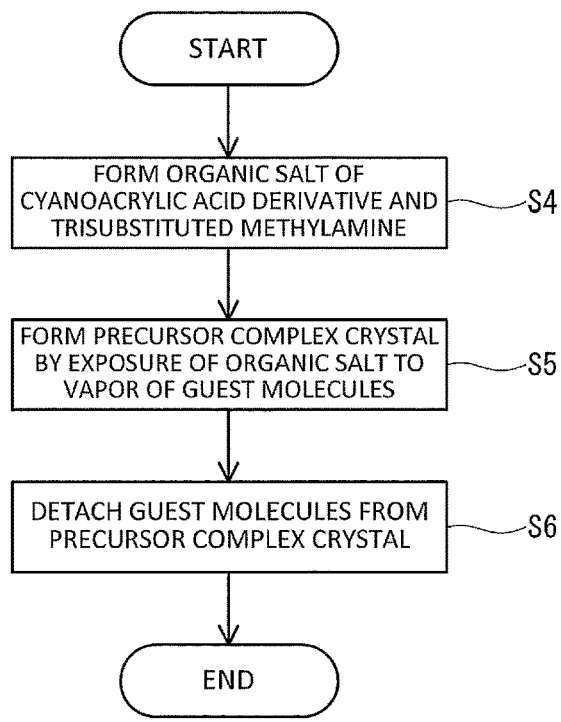
FIG. 7 shows an example of the method for producing the complex crystal according to the present disclosure.

FIG. 7 shows an example of the method for producing the complex crystal of the present disclosure. The method in FIG. 7 includes the following steps S4, S5, and S6. Step S4 is a step of forming the organic salt of the cyanoacrylic acid derivative and the trisubstituted methylamine. Step S5 is a step of forming a precursor complex crystal by exposing the organic salt formed in step S4 to vapor of the guest molecules 2. Step S6 is a step of forming the complex crystal of the present disclosure by detaching the guest molecules 2 from the precursor complex crystal formed in step S5.

[Chemosensor]

The chemosensor of the present disclosure includes the above-described complex crystal of the present disclosure and a detection unit that detects a characteristic of the complex crystal. The chemosensor of the present disclosure detects a predetermined chemical substance on the basis of a change in the characteristic detected by the detection unit.

The detection unit can include a light source that irradiates the complex crystal with light, and a light detector that detects light emitted from the complex crystal. In this case, with the light emitted from the complex crystal as the characteristic, the chemosensor of the present disclosure can detect the predetermined chemical substance on the basis of a change in the light. The change in the light is, for example, the difference between light emitted from the complex crystal in a first environmental condition and light emitted from the complex crystal in a second environmental condition. The first environmental condition and the second environmental condition are different from each other in concentration and/or type of the predetermined chemical substance. One condition selected from the first environmental condition and the second environmental condition can be an environmental condition of not containing the predetermined chemical substance.

Figure 8:
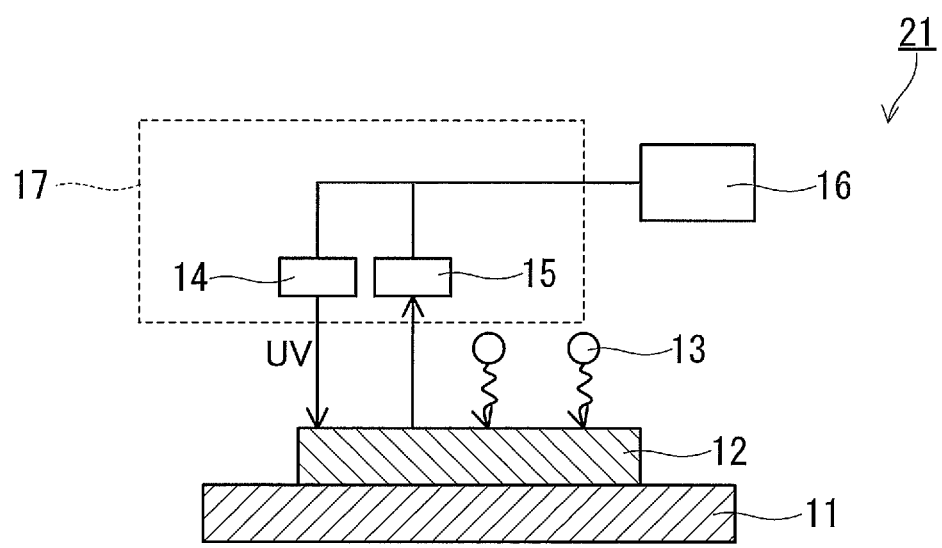
FIG. 8 is a schematic diagram showing an example of the configuration of the chemosensor according to the present disclosure.

FIG. 8 is a schematic diagram showing an example of the configuration of the chemosensor of the present disclosure. A chemosensor 21 in FIG. 8 is a sensor that detects a chemical substance 13. The chemosensor 21 includes a complex crystal 12 of the present disclosure and a detection unit 17 that detects a characteristic of the complex crystal 12. The complex crystal 12 is disposed on a substrate 11. The detection unit 17 is connected to a processing unit 16. The processing unit 16 controls the detection unit 17. In addition, the processing unit 16 evaluates the characteristic of the complex crystal 12 detected by the detection unit 17, and detects the chemical substance 13 on the basis of a change in the characteristic. The processing unit 16 can further determine information on the chemical substance 13. The information is, for example, type and/or concentration.

The detection unit 17 includes a light source 14 and a light detector 15. The light source 14 irradiates the complex crystal 12 with light. The light is, for example, light that allows the complex crystal 12 to emit fluorescence. The light is, for example, ultraviolet light (UV). The light detector 15 receives light emitted from the complex crystal 12. The received light is, for example, fluorescence emitted from the complex crystal 12. The processing unit 16 evaluates the light received by the light detector 15, as the characteristic of the complex crystal 12. The processing unit 16 detects the chemical substance 13 on the basis of a change in the light. The processing unit 16 can further determine information on the chemical substance 13.

The chemosensor 21 detects the predetermined chemical substance by using a change in the characteristic of the complex crystal 12 due to incorporation of the chemical substance 13. The chemosensor 21 detects the predetermined chemical substance, for example, by using a change in the fluorescence emitted from the complex crystal 12. For the evaluation by the processing unit 16, a more simplified change, for example, a change in at least one selected from the wavelength, the intensity, the brightness, the chromaticity, the lightness, and the saturation of the fluorescence can be used, instead of a change in fluorescence spectrum. The state of change in the characteristic of the complex crystal 12 can vary depending on the type and/or the concentration of the chemical substance 13 to be incorporated. The state detected by the detection unit 17 can be used for determining information on the chemical substance 13. For that purpose, the processing unit 16 can store data corresponding to information on the chemical substance 13 in advance. In this case, the processing unit 16 can determine information on the chemical substance 13 by comparing the state detected by the detection unit 17 with the data. The change in the characteristic can be evaluated on the basis of a difference and/or a rate of change.

In the example in FIG. 8, the light source 14 and the light detector 15 are disposed at the same surface side of the complex crystal 12. The light source 14 and the light detector 15 can be disposed such that the complex crystal 12 is sandwiched therebetween. In this case, the substrate 11 can be formed from a material that transmits the light emitted from the complex crystal 12.

The form of the complex crystal 12 on the substrate 11 is, for example, a film or a sheet. In this case, the thickness of the complex crystal 12 is, for example, 0.1 µm to 3000 µm.

The substrate 11 is formed from, for example, glass, quartz, silicon or an oxide thereof, a metal or an oxide thereof, a compound semiconductor, or a resin such as polytetrafluoroethylene and acrylic resin.

Known members can be used for the light source 14, the light detector 15, and the processing unit 16.

The detection unit 17 and the complex crystal 12 may be formed on the same substrate 11. When the light source 14 and the light detector 15 that are composed of semiconductor elements are used, the detection unit 17 and the complex crystal 12 can be integrally formed on a circuit board.

The chemosensor 21 can further include an optional member as long as detection of the chemical substance 13 is possible. The member is, for example, a member that introduces the chemical substance 13 to the complex crystal 12. In the case where the chemical substance 13 is contained in air, the member is, for example, a fan that sends air to the complex crystal 12.

The chemosensor of the present disclosure can use a change in a characteristic of the complex crystal 12 other than a change in fluorescence. The characteristic is, for example, at least one selected from an absorption spectrum, a reflection spectrum, an electrical resistance, and mass. The chemosensor of the present disclosure can include a detection unit 17 suitable for a characteristic in which a change is to be detected.

The chemosensor using a change in an absorption spectrum can have a structure that is the same as that of the chemosensor 21 in FIG. 8. The light source 14 emits light in the visible to ultraviolet region, for example.

The chemosensor using a change in a reflection spectrum can have a structure that is the same as that of the chemosensor 21 in FIG. 8. The light source 14 emits light in the visible to ultraviolet region, for example.

In the chemosensor using a change in an electrical resistance, the detection unit 17 includes, for example, a resistance measuring unit that measures the electrical resistance of the complex crystal 12. The resistance measuring unit can be a member that carries out a four-terminal resistance method.

The chemosensor using a change in an electrical resistance includes, for example, a field effect transistor (FET) having a region composed of the complex crystal 12. In a specific example, the chemosensor includes a FET in which the region is formed between a gate electrode and a gate insulating film. This FET detects the electric resistance of the region changed due to incorporation of the chemical substance.

The chemosensor using a change in mass includes, for example, a quartz crystal microbalance sensor (hereinafter, a QCM sensor). The QCM sensor is a sensor that includes a quartz oscillator and that is capable of measuring an extremely small change in mass. The QCM sensor is disclosed, for example, in Japanese Laid-Open Patent Publication No. 2009-236607. In a more specific example, the chemosensor includes a QCM sensor in which a region composed of the complex crystal 12 is formed on the surface of the quartz oscillator. The QCM sensor detects a change in mass of the region due to incorporation of the chemical substance.

The chemosensor using a change in mass includes, for example, a membrane-type surface stress sensor (hereinafter, an MSS sensor). The MSS sensor has a minute plate-like member supported by a connection portion having piezo resistance, and a receptor layer provided on the surface of the plate-like member. The MSS sensor can measure an extremely small change in mass. The MSS sensor is disclosed, for example, in International Publication No. WO 2011/148774. In a more specific example, the chemosensor includes an MSS sensor in which a region composed of the complex crystal 12 is formed on the surface of the plate-like member. The MSS sensor detects a change in mass of the region due to incorporation of the chemical substance.

EXAMPLES

Hereinafter, the complex crystal and the chemosensor of the present disclosure will be more specifically described based on examples. The complex crystal and the chemosensor of the present disclosure are not limited to the following examples.

Example 1 and Comparative Example 1

In a three-necked flask with an internal volume of 300 mL, 5.00 g (21.5 mmol) of 4-methoxy-N-phenylaniline, 5.57 g (30.1 mmol) of 4-bromobenzaldehyde, and 150 mL of toluene were put. Next, under stirring, 0.225 g (1.00 mmol) of $Pd(OAc)_2$, 0.406 g (2.01 mmol) of $t-Bu_3P$, and 5.20 g (37.6 mmol) of potassium carbonate were added, and the mixture was heated to carry out heating reflux for 20 hours. Next, the solution was cooled to room temperature, the insoluble matter was removed by celite filtration, and then the filtrate was concentrated under reduced pressure. Next, the obtained residue was purified by silica gel column chromatography to obtain 5.74 g of 4-((4-methoxyphenyl)(phenyl)amino)benzaldehyde.

Next, in an eggplant-shaped flask with an internal volume of 200 mL, 5.73 g (18.89 mmol) of the obtained 4-((4-methoxyphenyl)(phenyl)amino)benzaldehyde, 2.41 g (28.33 mmol) of cyanoacetic acid, and 50 mL of acetonitrile were put, and 3.74 mL of piperidine was poured thereinto under stirring. Then, the mixture was heated to carry out heating reflux for 1 hour. Next, the solution was cooled to room temperature, the precipitated crystal was collected by filtration, and the collected crystal was suspended in 150 mL of water. Next, under stirring, a sodium carbonate aqueous solution was added to adjust the pH to 10 or higher. Then, diluted hydrochloric acid was added to adjust the pH to 4, and the crystal was collected by filtration and dried under reduced pressure to obtain 6.12 g of (E)-2-cyano-3-(4-((4-methoxyphenyl)(phenyl)amino)phenyl)acrylic acid.

Next, at room temperature, (E)-2-cyano-3-(4-((4-methoxyphenyl)(phenyl)amino)phenyl)acrylic acid and triphenylmethylamine were mixed in methanol at a molar ratio of 1:1. Then, the methanol was removed under reduced pressure to form an organic salt.

Next, the formed organic salt was dissolved in a solvent obtained by mixing chloroform and diethyl ketone at a volume ratio of 4:1, and allowed to stand at room temperature for 48 hours to cause recrystallization, to obtain a particulate precursor complex crystal. The following items (1) to (3) were confirmed for the formed precursor complex crystal by thermogravimetric analysis, XRD measurement, and $^1$H-NMR measurement (reference substance: tetramethylsilane (TMS); the same applies below).

(1) The organic salt is an organic salt of (E)-2-cyano-3-(4-((4-methoxyphenyl)(phenyl)amino)phenyl)acrylic acid and triphenylmethylamine (2) The precursor complex crystal has a structure in which supramolecular units that are the organic salt, and chloroform and diethyl ketone that are guest molecules are arrayed.

(3) The content of the guest molecules in the precursor complex crystal is nearly equal to the theoretical maximum value derived from the above confirmed array.

Figure 9:
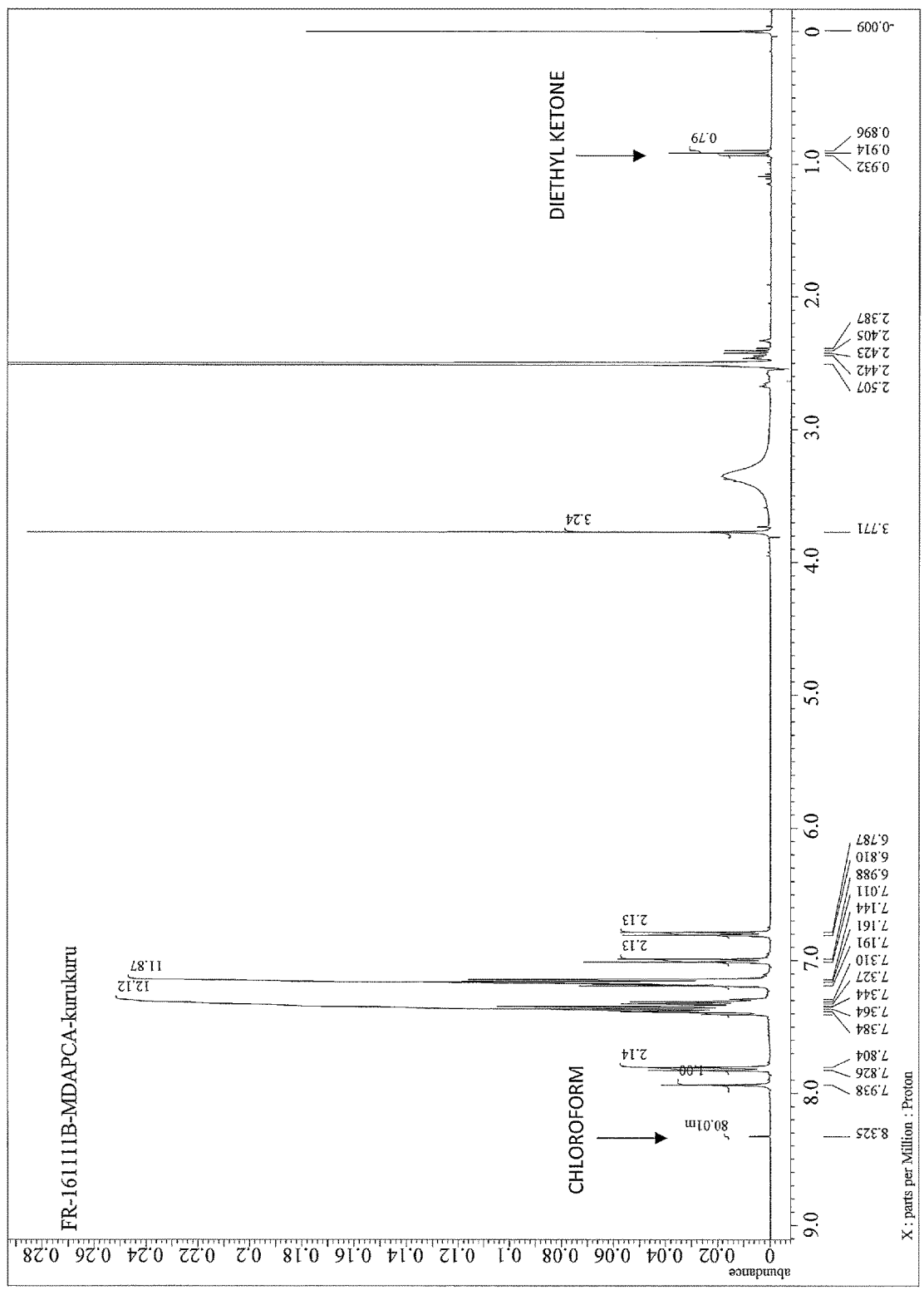
FIG. 9 is a diagram showing a $^1$H-nuclear magnetic resonance (NMR) profile for a precursor complex crystal produced in Example 1.

FIG. 9 is a diagram showing a $^1$H-NMR profile of the precursor complex crystal of Example 1. In the profile, a peak at a chemical shift of 0.89 ppm is a peak of diethyl ketone, and a peak at a chemical shift of 8.32 ppm is a peak of chloroform.

Next, the precursor complex crystal was treated with supercritical carbon dioxide to detach the guest molecules from the crystal. In this manner, a complex crystal of Example 1 was obtained. The obtained complex crystal had maintained the form of the precursor complex crystal. The following items (1) to (5) were confirmed for the formed complex crystal by XRD measurement and $^1$H-NMR measurement.

(1) The complex crystal has a structure in which supramolecular units that are the organic salt are arrayed.

(2) The array of the supramolecular units maintains the array of the supramolecular units in the precursor complex crystal.

(3) Molecular cavities are formed between the supramolecular units.

(4) The array of the molecular cavities coincides with the array of the guest molecules in the precursor complex crystal.

(5) The content of the guest molecules in the complex crystal was equal to or less than the measurement limit of NMR, that is, less than 1 mol %, and the cavity rate of the complex crystal was equal to or greater than 99%.

Figure 10:
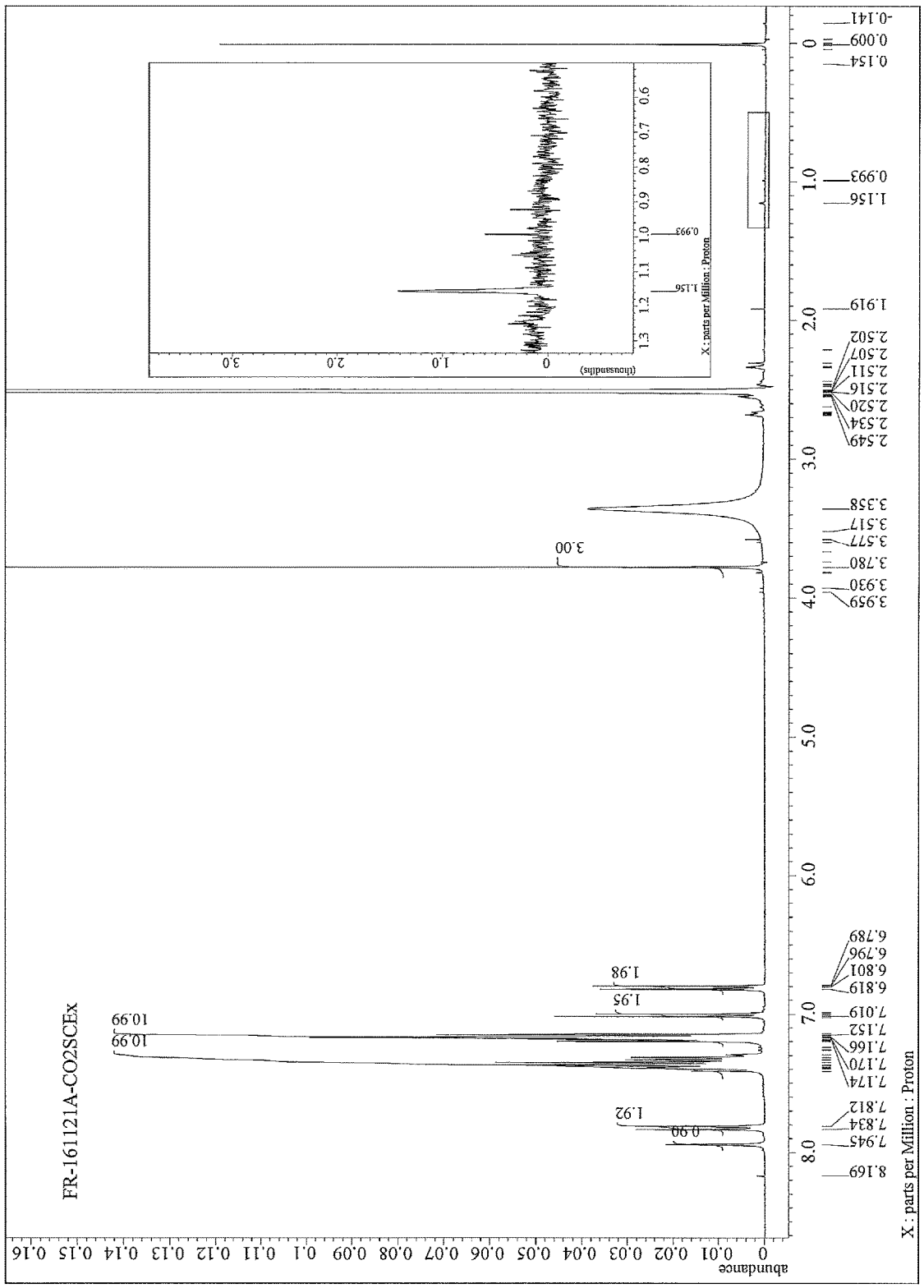
FIG. 10 is a diagram showing a $^1$H-NMR profile for a complex crystal produced in Example 1.
Figure 11:
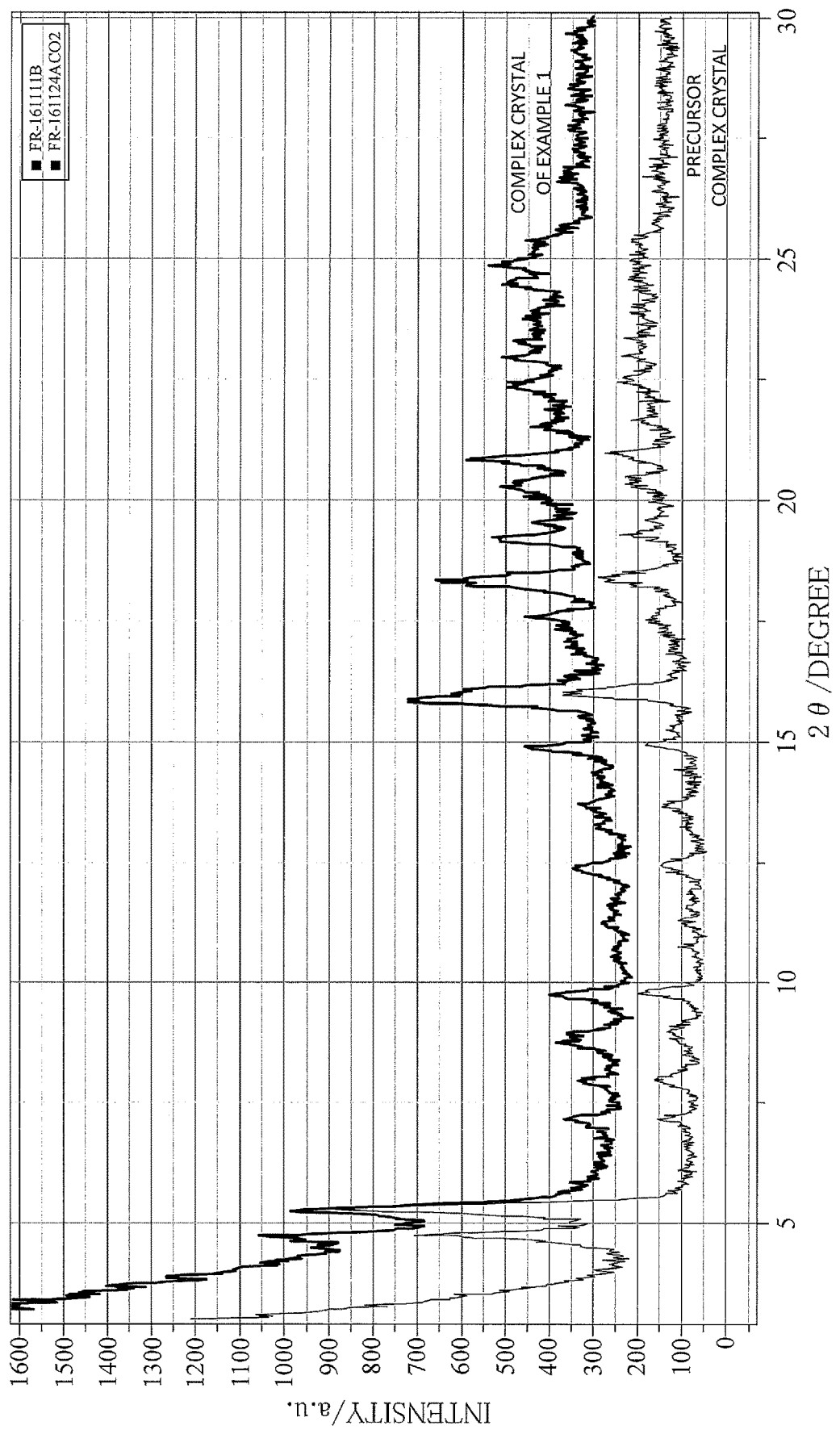
FIG. 11 is a diagram showing X-ray diffraction (XRD) profiles for the precursor complex crystal and the complex crystal produced in Example 1.

FIG. 10 is a diagram showing a $^1$H-NMR profile of the complex crystal of Example 1. In the profile, peaks of diethyl ketone and chloroform are not present. FIG. 11 is a diagram showing XRD profiles of the complex crystal and the precursor complex crystal of Example 1. From the profiles, it is confirmed that both crystals have peaks at the same diffraction angle 2θ. That is, it was confirmed that both crystals have the same crystal structure except for presence/absence of guest molecules.

Next, the complex crystal of Example 1 was exposed to ammonia gas at a concentration of 10 ppm (volume basis; the same applies below), and a change in two-dimensional fluorescence intensity (a change before and after the exposure) exhibited by the complex crystal was evaluated. The evaluation was carried out according to the following procedure.

1. Particles of the complex crystal were placed on a sample stage. Then, the sample stage was stored in a gas flow cell. The gas flow cell was equipped with a window, a gas inlet, and a gas outlet. The window was sized and located such that it was possible to irradiate the particles on the sample stage with light and it was possible to detect fluorescence emitted by the particles.

2. Before introducing ammonia gas into the gas flow cell, a fluorescence intensity A of the complex crystal was measured. Specifically, the complex crystal was irradiated with ultraviolet light having a wavelength of 365 nm, and fluorescence emitted by the crystal at that time was photographed by a camera (FLOYD manufactured by WRAYMER) to obtain a fluorescence intensity A.

3. Ammonia gas diluted to a concentration of 10 ppm with nitrogen was introduced into the gas flow cell, and the complex crystal was exposed to the gas. After 10 minutes from the start of exposure, a fluorescence intensity B of the complex crystal was measured. The measurement of the fluorescence intensity B was performed in the same manner as the measurement of the fluorescence intensity A.

4. By image processing, the differential intensity between the fluorescence intensity A and the fluorescence intensity B was obtained. The differential intensity was a value obtained by subtracting a relatively smaller intensity from a relatively larger intensity selected from the fluorescence intensity A and the fluorescence intensity B.

Next, a change in two-dimensional fluorescence intensity when the precursor complex crystal was exposed to the ammonia gas at a concentration of 10 ppm was evaluated by the same procedure (Comparative Example 1).

From these evaluations, a greater change in fluorescence intensity was confirmed in the complex crystal of Example 1 from which the guest molecules were detached, as compared to the precursor complex crystal of Comparative Example 1 from which the guest molecules were not detached. That is, it was confirmed that the complex crystal of Example 1 exhibits higher fluorescence responsiveness to a chemical substance as compared to the precursor complex crystal of Comparative Example 1.

Figure 12A:
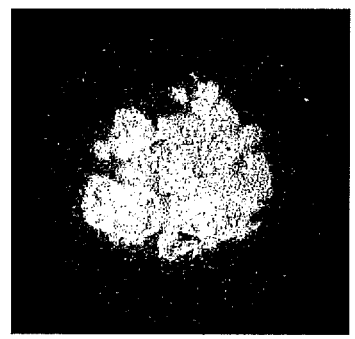
FIG. 12A is a diagram showing differential intensity obtained for the complex crystal according to Example 1.
Figure 12B:
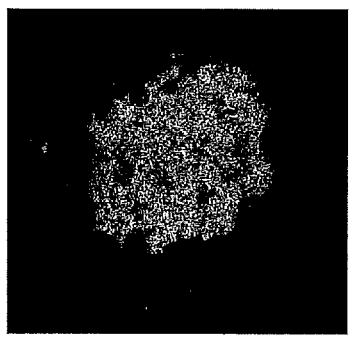
FIG. 12B is a diagram showing differential intensity obtained for a complex crystal according to Comparative Example 1.

The differential intensities obtained in Example 1 and Comparative Example 1 are shown in FIG. 12A and FIG. 12B. FIG. 12A shows the differential intensity in Example 1. FIG. 12B shows the differential intensity in Comparative Example 1.

Comparative Example 2

At room temperature, anthracene divinylsulfonic acid and triphenylmethylamine were mixed in methanol at a molar ratio of 1:2. Then, the methanol was removed under reduced pressure to form an organic salt. Anthracene divinylsulfonic acid is represented by the following formula (3).

[Chem. 5]

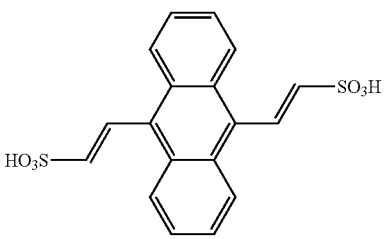

(3)

Next, the formed organic salt was dissolved in a solvent obtained by mixing methanol and 1,2-dichloroethane at a volume ratio of 3:4, and allowed to stand at room temperature for 48 hours to cause recrystallization, to obtain a particulate precursor complex crystal. The following items (1) to (3) were confirmed for the formed precursor complex crystal by thermogravimetric analysis, XRD measurement, and $^1$H-NMR measurement.

(1) The organic salt is an organic salt of anthracene divinylsulfonic acid and triphenylmethylamine (2) The precursor complex crystal has a structure in which supramolecular units that are the organic salt and 1,2-dichloroethane that is guest molecules derived from the mixed solvent are arrayed.

(3) The content of the guest molecules in the precursor complex crystal is nearly equal to the theoretical maximum value derived from the above confirmed array.

Next, the precursor complex crystal was treated with supercritical carbon dioxide to detach the guest molecules from the crystal. In this manner, a complex crystal of Comparative Example 2 was obtained. The obtained complex crystal had maintained the form of the precursor complex crystal. The following items (1) to (5) were confirmed for the formed complex crystal by XRD measurement and $^1$H-NMR measurement.

(1) The complex crystal has a structure in which supramolecular units that are the organic salt are arrayed.

(2) The array of the supramolecular units maintains the array of the supramolecular units in the precursor complex crystal.

(3) Molecular cavities are formed between the supramolecular units.

(4) The array of the molecular cavities coincides with the array of the guest molecules in the precursor complex crystal.

(5) The content of the guest molecules in the complex crystal was equal to or less than the measurement limit of NMR, that is, less than 1 mol %.

Next, a change in two-dimensional fluorescence intensity when the complex crystal of Comparative Example 2 was exposed to ammonia gas at a concentration of 10 ppm was evaluated in the same manner as Example 1.

Figure 13:
FIG. 13 is a diagram showing differential intensity obtained for a complex crystal according to Comparative Example 2.

From this evaluation, it was confirmed that in the complex crystal of Comparative Example 2, a change in fluorescence intensity due to the exposure to the ammonia gas hardly occurs. That is, it was confirmed that the complex crystal of Example 1 exhibits significantly higher fluorescence responsiveness to a chemical substance as compared to the complex crystal of Comparative Example 2. The differential intensity obtained in Comparative Example 2 is shown in FIG. 13.

Comparative Example 3

At room temperature, stilbene-4,4'-disulfonic acid and triphenylmethylamine were mixed in methanol at a molar ratio of 1:2. Then, the methanol was removed under reduced pressure to form an organic salt. Stilbene-4,4'-disulfonic acid is represented by the following formula (4).

[Chem. 6]

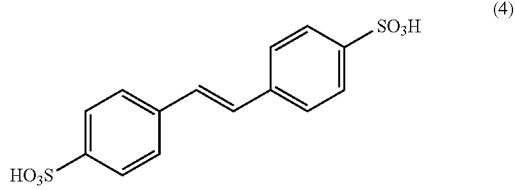

(4)

Next, the formed organic salt was dissolved in a solvent obtained by mixing methanol and o-chlorotoluene at a volume ratio of 1:2, and allowed to stand at room temperature for 48 hours to cause recrystallization, to obtain a particulate precursor complex crystal. The following items (1) to (3) were confirmed for the formed precursor complex crystal by thermogravimetric analysis, XRD measurement, and $^1$H-NMR measurement.

(1) The organic salt is an organic salt of stilbene-4,4'-disulfonic acid and triphenylmethylamine (2) The precursor complex crystal has a structure in which supramolecular units that are the organic salt and o-chlorotoluene that is guest molecules derived from the mixed solvent are arrayed.

(3) The content of the guest molecules in the precursor complex crystal is nearly equal to the theoretical maximum value derived from the above confirmed array.

Next, the precursor complex crystal was treated with supercritical carbon dioxide to detach the guest molecules from the crystal. In this manner, a complex crystal of Comparative Example 3 was obtained. The obtained complex crystal had maintained the form of the precursor complex crystal. The following items (1) to (5) were confirmed for the formed complex crystal by XRD measurement and $^1$H-NMR measurement.

(1) The complex crystal has a structure in which supramolecular units that are the organic salt are arrayed.

(2) The array of the supramolecular units maintains the array of the supramolecular units in the precursor complex crystal.

(3) Molecular cavities are formed between the supramolecular units.

(4) The array of the molecular cavities coincides with the array of the guest molecules in the precursor complex crystal.

(5) The content of the guest molecules in the complex crystal was equal to or less than the measurement limit of NMR, that is, less than 1 mol %.

Next, a change in two-dimensional fluorescence intensity when the complex crystal of Comparative Example 3 was exposed to ammonia gas at a concentration of 10 ppm was evaluated in the same manner as Example 1.

Figure 14:
FIG. 14 is a diagram showing differential intensity obtained for a complex crystal according to Comparative Example 3.

From this evaluation, it was confirmed that in the complex crystal of Comparative Example 3, a change in fluorescence intensity due to the exposure to the ammonia gas does not occur. That is, it was confirmed that the complex crystal of Example 1 exhibits significantly higher fluorescence responsiveness to a chemical substance as compared to the complex crystal of Comparative Example 3. The differential intensity obtained in Comparative Example 3 is shown in FIG. 14.

Example 2

A change in fluorescence intensity when the complex crystal of Example 1 was exposed to ammonia gas at each of predetermined evaluation concentrations was evaluated in the same manner as Example 1. It should be noted that, in "procedure 3" described in Example 1, gas diluted to each evaluation concentration with nitrogen was introduced into the gas flow cell, and the complex crystal was exposed to the gas. The evaluation concentrations were 0.05 ppm, 0.1 ppm, 0.25 ppm, and 0.5 ppm. The evaluation was carried out for each evaluation concentration with the number of samples n=3.

Figure 15:
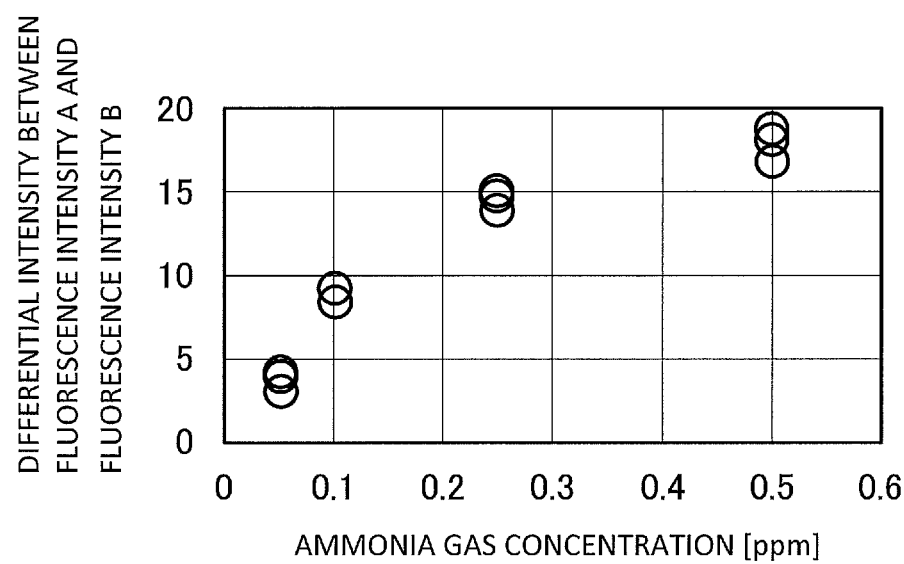
FIG. 15 is a diagram showing the gas concentration dependency of differential intensity with respect to ammonia gas in a complex crystal according to Example 2.

The evaluation results of the differential intensity obtained in Example 2 are shown in FIG. 15. The normalized differential intensity shown in FIG. 15 was obtained by performing the following image processing using image editing software (Photoshop CS2 manufactured by Adobe Systems Co., Ltd.) on an image showing two-dimensional differential intensity obtained in the same manner as Example 1.

First, a region corresponding to complex crystal particles is selected from the image. The region to be selected is such that among the complex crystal particles that can be viewed in the image, particles, the number of which is at least 60% and preferably about 80% of the number of the complex crystal particles, are included. The region to be selected is such that the region not corresponding to the particles (the region in which the sample stage is viewed) is not included as much as possible, and the proportion of the region not corresponding to the particles in the selected region does not exceed 3% on a surface area basis. When an image showing two-dimensional differential intensity is in color, the image is converted to gray scale in advance.

Next, the brightness value for each pixel is extracted for the selected range, and the average value of the extracted brightness values is set as the normalized differential intensity. The brightness value is a value based on 256 gradations where black is 0 and white is 255.

As shown in FIG. 15, in the complex crystal of Example 2, a great change in fluorescence intensity was confirmed for ammonia gas at a concentration of 0.5 ppm or lower. In addition, it was confirmed that the complex crystal of Example 2 exhibits fluorescence responsiveness in which the differential intensity changes depending on the concentration of the ammonia gas.

The complex crystal and the chemosensor of the present disclosure are not limited to each embodiment described above, and various modifications and changes may be made without departing from the scope of the invention recited in the claims. For example, the technical features shown in the embodiments described in DESCRIPTION OF EMBODIMENTS may be replaced or combined as appropriate in order to solve a part or all of the above-described problems or to achieve a part or all of the above-described effects. Moreover, the technical features may be deleted as appropriate unless described as essential in the present specification.

INDUSTRIAL APPLICABILITY

The complex crystal of the present disclosure can be applied to, for example, a chemosensor that detects a chemical substance.

The invention claimed is:

1. A complex crystal having a structure in which supramolecular units each composed of two or more types of molecules are arrayed, wherein
    each of the supramolecular units contains a cyanoacrylic acid derivative and a trisubstituted methylamine as the molecules,
    the complex crystal has, between the supramolecular units adjacent to each other:
        a guest molecule for which the supramolecular unit is a host; and
        molecular cavities in each of which the guest molecule for which the supramolecular unit is the host is not disposed, and
        a content of the guest molecules is 1 mol % or less.

2. The complex crystal according to claim 1, wherein the cyanoacrylic acid derivative is a compound represented by the following formula (1),

[Chem. 1]

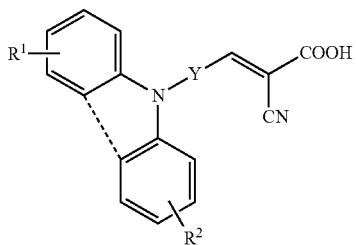

wherein Y is a phenylene group, a naphthylene group, a pyridinylene group, a thiophenylene group, or a furanylene group, each group may have a substituent, $R^1$ and $R^2$ are each independently a hydrogen atom, a hydroxyl group, a methoxy group, an ethoxy group, a methyl group, an ethyl group, a propyl group, an isopropyl group, an amino group, a cyano group, an aldehyde group, a thiol group, a vinyl group, a nitro group, a halogen atom, a carboxy ester group, an N-substituted amide group, a phenyl group, a naphthyl group, a pyridyl group, a thiophenyl group, or a furanyl group, the compound represented by formula (1) may or may not have a bond at a broken line portion in formula (1), and, when the compound has a bond, the bond is a single bond, —$CH_2$—, —O—, —S—, or —NH—.

3. The complex crystal according to claim 1, wherein the trisubstituted methylamine is a compound represented by the following formula (2),

[Chem. 2]

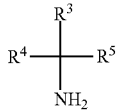

wherein $R^3$ to $R^5$ are each independently a phenyl group, a naphthyl group, a pyridyl group, a thiophenyl group, or a furanyl group, and each group may have a substituent.

4. The complex crystal according to claim 1, wherein the complex crystal is obtained by detaching the guest molecules from a precursor complex crystal having a structure in which the supramolecular units and the guest molecules are arrayed, by supercritical drying using supercritical carbon dioxide.

5. A chemosensor comprising:
the complex crystal according to claim 1; and
a detection unit configured to detect a characteristic of the complex crystal, wherein
the chemosensor detects a predetermined chemical substance on the basis of a change in the characteristic detected by the detection unit.

6. The chemosensor according to claim 5, wherein
the detection unit includes a light source configured to irradiate the complex crystal with light, and a light detector configured to detect light emitted from the complex crystal, and
with the light emitted from the complex crystal as the characteristic, the chemosensor detects the predetermined chemical substance on the basis of a change in the light.

7. The chemosensor according to claim 6, wherein the change in the light is a difference between light emitted from the complex crystal in a first environmental condition and light emitted from the complex crystal in a second environmental condition.

8. A method for producing the complex crystal according to claim 1, the method comprising
detaching the guest molecules from a precursor complex crystal having a structure in which the supramolecular units and the guest molecules are arrayed, to form the complex crystal, wherein
the detachment of the guest molecules from the precursor complex crystal is carried out by supercritical drying using supercritical carbon dioxide, and
the complex crystal has, between the supramolecular units adjacent to each other:
the guest molecules for which the supramolecular unit is the host and
the molecular cavities in each of which the guest molecule for which the supramolecular unit is the host is not disposed, and
the content of the guest molecules is 1 mol % or less.

9. The complex crystal according to claim 1, wherein a cavity rate of the complex crystal is equal to or greater than 70%, wherein the cavity rate is a ratio of a number of the molecular cavities in which the guest molecules are not disposed to a sum of a number of the guest molecules and the number of the cavities in which the guest molecules are not disposed.

* * * * *